United States Patent [19]

Coppa et al.

[11] Patent Number: 4,553,841
[45] Date of Patent: Nov. 19, 1985

[54] METHOD OF AND APPARATUS FOR MEASURING THICKNESS AND REFRACTIVE INDEX OF TRANSPARENT BODIES

[75] Inventors: Gianni Coppa, Asti; Giorgio Grego, Turin, both of Italy

[73] Assignee: Cselt Centro Studi E Laboratori Telecomunicazioni, S.p.A., Turin, Italy

[21] Appl. No.: 465,031

[22] Filed: Feb. 8, 1983

[30] Foreign Application Priority Data

Feb. 10, 1982 [IT] Italy ............................ 67149 A/82

[51] Int. Cl.$^4$ ............................................. G01B 9/02
[52] U.S. Cl. .................................. 356/349; 356/73.1; 356/357; 356/361
[58] Field of Search ...................... 356/73.1, 349, 357, 356/361

[56] References Cited

U.S. PATENT DOCUMENTS 3,471,238 10/1969 Hawke ............................. 356/349
4,441,811 4/1984 Melezoglu et al. ............. 356/73.1 X
4,492,463 2/1985 Marcuse et al. ................... 356/73.1

OTHER PUBLICATIONS

Goodman, "Optical Interference Method . . . ", *Applied Optics*, vol. 17, No. 17, p. 2779, Sep. 1978.
Koronkevich et al., "Interference Microscope with a Frequency Shift . . . ", *Sou. J. Quant. Electr.*, vol. 9, No. 10, p. 1332, Oct. 1979.
Article entitled "Fundamentals of Optics", by Francis A. Jenkins, and Harvey E. White, pp. 16–22.

*Primary Examiner*—Davis L. Willis
*Assistant Examiner*—Matthew W. Koren
*Attorney, Agent, or Firm*—Karl F. Ross; Herbert Dubno

[57] ABSTRACT

A body transparent to laser radiation, such as an optical fiber or a preform thereof in the process of manufacture, is transluminated by a monochromatic beam of a frequency in the THz range split off from a composite laser beam with two closely spaced frequencies produced by the Zeeman effect. Another monochromatic beam of the second laser frequency bypasses the transparent body and is photoelectrically recombined with the first beam to provide an electrical measuring wave at a beat frequency in the MHz range differing in phase from an electrical reference wave of the same beat frequency, similarly derived from the original laser beam, to an extent determined by the refractive index and the thickness of the transluminated body. Two or more phase comparisons are made with different angles of incidence of the transluminating beam and their results are compared for an arithmetic determination of refractive index and thickness.

18 Claims, 2 Drawing Figures

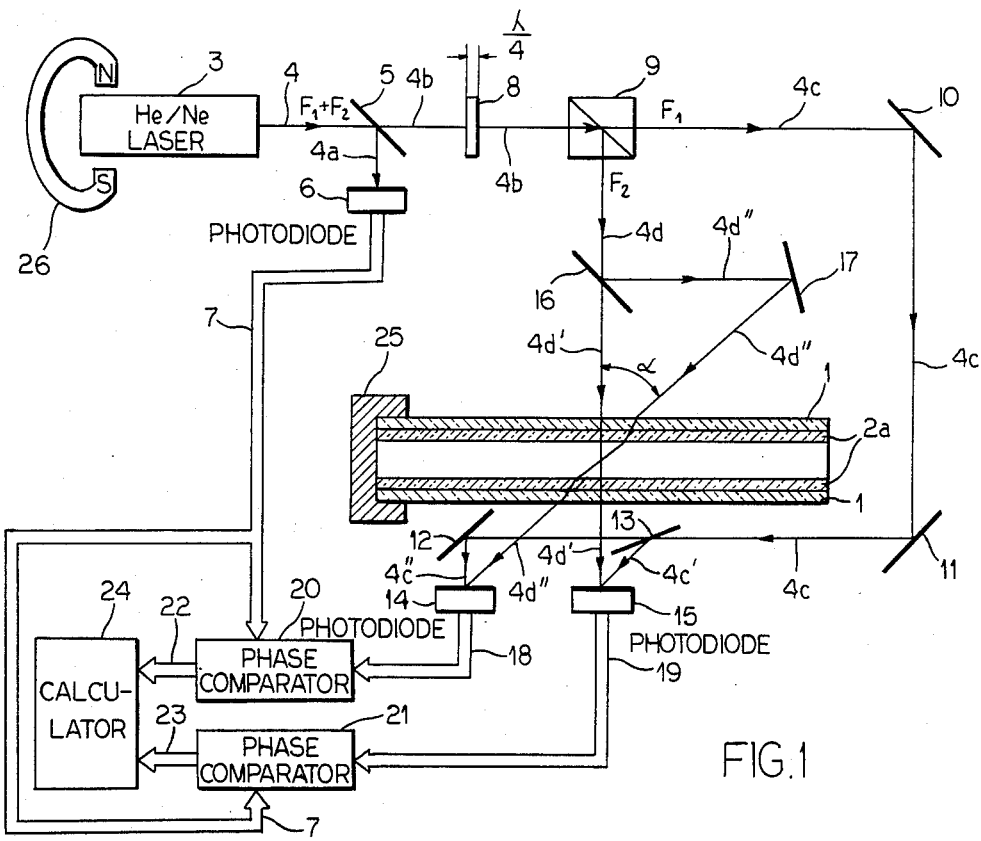
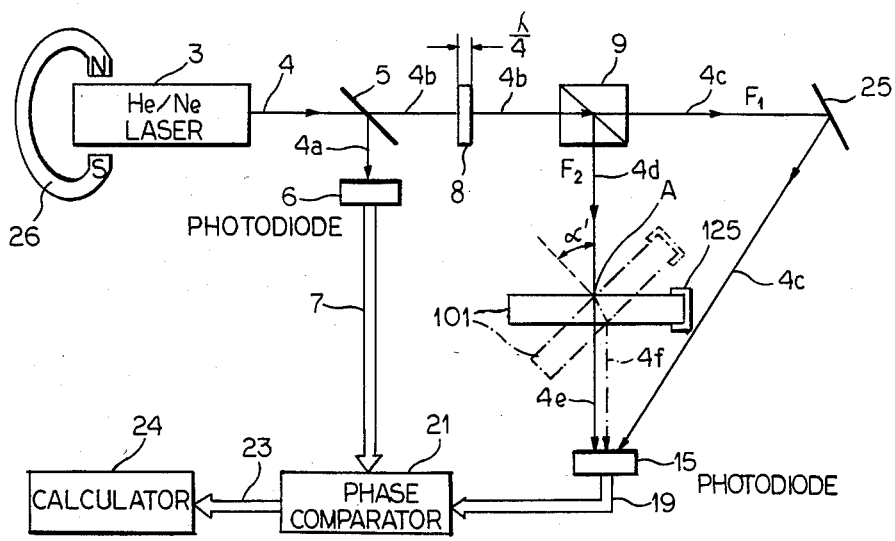
FIG.2

METHOD OF AND APPARATUS FOR MEASURING THICKNESS AND REFRACTIVE INDEX OF TRANSPARENT BODIES

FIELD OF THE INVENTION

Our present invention relates to a method of measuring the thickness and the refractive index of a transparent body as well as to an apparatus for carrying out this method.

BACKGROUND OF THE INVENTION

Various systems are known for measuring the refractive index of a test object, e.g. an optical fiber or a preform used in its manufacture, in order to determine whether that index conforms to existing requirements. Devices used for this purpose include refractometers of the Pulfrich and Abbe types as well as spectrometers; see, for example, pages 17, 22 and 23 of "Fundamentals of Optics" by Francis A. Jenkins and Harvey E. White, published 1957 by McGraw-Hill Book Company, Inc.

All these conventional devices are limited to samples of certain shape (e.g. prismatic) taken from the body to be tested. Thus, they cannot be utilized for the continuous measurement of the refractive index of a body in production, e.g. an optical preform manufactured by the coating of an inner or outer cylindrical surface of a vitreous support with a similar material in a succession of layers, as by the technique of chemical-vapor deposition (CVD). Nor do these devices facilitate the determination of the thickness of the transparent body or layer of interest.

It has already been proposed to determine the refractive index of a preform during manufacture thereof by measuring its surface temperature. Such a method, of course, requires the surface being coated to be accessible and can therefore not be employed when the vitreous material is being deposited on the inner surface of a tubular support. Again, there is no possibility with this method to determine the thickness of the coating or of any layer thereof.

OBJECTS OF THE INVENTION

An important object of our present invention, therefore, is to provide a method of conveniently and nondestructively measuring both the thickness and the refractive index of a transparent body, i.e. without requiring the removal of a test sample therefrom.

A related object is to provide a simple and relatively inexpensive apparatus for performing that method.

A more particular object of our invention is to provide a method and an apparatus of the character referred to which can be applied to optical fibers and to their preforms during manufacture.

SUMMARY OF THE INVENTION

Our invention is applicable to any test object or workpiece, transparent to luminous radiation, with substantially parallel major surfaces which either are planar or are curved with a radius that is large in comparison to the wavelength of such radiation. When such a test object is transluminated with monochromatic rays at various angles of incidence, the effective length of the ray path—which is a function of the thickness and the refractive index—changes in dependence upon that angle. The change in path length brings about a phase shift of the transluminating rays relatively to one another as well as to rays which do not traverse the test object. While such a phase shift at the frequencies here involved—in the THz range—cannot be measured directly with equipment currently available, we have found that its extent can be determined by photoelectrically mixing two monochromatic light rays of slightly different frequencies to produce an electrical wave of substantially lower frequency, i.e. a beat frequency preferably lying in the low MHz range, yielding the required information.

Thus, the method of our invention essentially comprises the steps of (a) generating a first and a second monochromatic beam of luminous radiation of constant frequencies differing slightly from each other, (b) photoelectrically deriving from these beams an electrical reference of the aforementioned beat frequency corresponding to the difference between the two beam frequencies, (c) transluminating the test object with rays of the second beam at a first angle of incidence, (d) photoelectrically mixing rays of this second beam—passed by the test object—with rays of the first beam—traveling over a different path—to derive therefrom a first electrical measuring wave of the same beat frequency as the reference wave but differing therefrom in phase, (e) determining the phase difference between the reference wave and the first measuring wave, (f) repeating the foregoing steps (c) and (d) with a second angle of incidence— differing from the first angle—to derive from rays of the two beams a second electrical measuring wave of the same beat frequency also differing in phase from the reference wave, (g) determining the phase difference between the reference wave and the second measuring wave, and (h) calculating the thickness and the refractive index of the test object from the values obtained in the foregoing steps (e) and (g).

In order to insure the requisite constancy of the beam frequencies, we prefer to obtain them from a common laser subjected to a magnetic field which produces the well-known Zeeman effect resulting in the generation of a composite beam whose constituents are the two monochromatic beams whose frequencies may differ by only a few MHz; these constituent beams, when emitted by the laser, are circularly polarized with opposite directions of rotation and can thus be readily separated by means well known in the art, preferably a quarter-wave plate followed by a polarizer. The frequency-separating means are part of an optical system designed to guide rays of the first beam along a first path and rays of the second beam along a second and a third path, the latter respectively traversing the test object at the first and the second angle of incidence referred to above. The electrical reference wave is produced by first photoelectric means positioned to receive rays of both monochromatic beams while rays from the first, second and third paths impinge upon second photoelectric means producing the aforementioned measuring waves. The phase differences between the reference wave and the two measuring waves are determined by phase-comparison means connected to the first and second photoelectric means, the phase-comparison means working into arithmetic means serving to calculate the two unknown parameters of interest—namely the thickness and the refractive index of the test object—from these two phase differences.

Reference may be made to a commonly owned application of even date filed by one of us, Giorgio Grego, under Ser. No. 465,014, disclosing the use of such a Zeeman-effect laser for the determination of the refractive-index profile of an optical fiber or preform.

The two measuring waves can be produced either simultaneously or successively. In the first instance, rays from the second beam are concurrently transmitted through the test object as the first and second angles of incidence referred to. In the second instance, the transluminating rays of the second beam are directed by suitable optical means—such as the aforementioned polarizer—onto a trajectory transverse to an axis about which the test object is relatively swingable, as by being mounted on a holder rotatable about that axis; the second and third ray paths then branch off from that trajectory in respective angular positions of the test object and its holder.

It will generally be convenient to make the angle of incidence zero for the first measuring wave, i.e. for the rays of the second beam traveling over the second path. We also prefer to let the ray path of the first beam bypass the test object so that the phase of these rays at the point of mixture with those of the second beam—i.e. at the receiving surface of a photodetector—will be constant. The same applies to the rays of the two beams used for generating the reference wave.

BRIEF DESCRIPTION OF THE DRAWING

The above and other features of our invention will now be described in detail with reference to the accompanying drawing in which:

FIG. 1 is a diagram illustrating the application of our invention to the measurement of thickness and refractive index of layers deposited on the inner surface of a vitreous supporting tube in the formation of a fiber-optical preform; and FIG. 2 is a diagram similar to that of FIG. 1 but illustrating a modification applied to a different kind of test object.

SPECIFIC DESCRIPTION

In the drawing, single lines are used for ray paths whereas double-line arrows denote electrical connections.

FIG. 1 schematically represents an apparatus according to our invention designed to measure the thickness and the refractive index of a test object or workpiece comprising a cylindrical supporting tube 1 of silica glass on which layers 2a of similar vitreous material (only one shown), specifically doped silica, are being deposited from a vapor phase by a nonillustrated nozzle reciprocating axially within the continuously rotating tube. The latter is shown mounted in a holder 25 which is rotated about the tube axis by means likewise not shown. After the deposition of the internal layers 2a has been completed, the resulting workpiece including tube 1 constitutes a preform for the drawing of an optical fiber as is well known in the art.

A source of light rays, specifically a laser 3 of the He/Ne type, is disposed in the field of a permanent magnet 26 in order to emit a composite beam 4 consisting of two monochromatic radiations of frequencies $F_1$ and $F_2$ generated by the Zeeman effect. The two radiations, which are circularly polarized with opposite senses of rotation, lie in the THz range and differ from each other by a beat frequency of about 2 MHz. Typically, the order of magnitude of these two laser frequencies is 275 THz.

A beam splitter 5 directs a part 4a of composite beam 4 onto a photodiode 6 which, in response to the beat frequency of the constituent radiations, delivers an electrical reference wave of frequency $|F_1-F_2|$ on a lead 7 to respective inputs of two phase comparators 20 and 21. The remainder 4b of beam 4 traverses a quarter-wave plate 8 converting the circular polarization of frequencies $F_1$ and $F_2$ into linear polarization in two orthogonal planes. A polarizer 9 separates these two radiations from each other, directing a first beam 4c of frequency $F_1$ onto a path bypassing the test object 1, 2a while deviating a second beam 4d of frequency $F_2$ toward that test object. Beam 4c travels on a first path, defined by reflectors 10 and 11, toward a further beam splitter 13 directing a part 4c' thereof onto a photodiode 15 and another part 4c'' thereof by way of an additional reflector 12 onto another diode 14. A further beam splitter 16 divides the beam 4d into two branches 4d' and 4d'', the former transluminating the test object 1, 2a on a second path perpendicular to its axis to impinge upon photodiode 15 while the latter is trained by a reflector 17 onto a third path which also traverses the test object and terminates at photodiode 14, this third path including an angle of incidence $\alpha$ with the transverse direction represented by the path of ray bundle 4d'. Photodiodes 14 and 15 generate respective measuring waves which have the same beat frequency as that produced by photodiode 6 but differ therefrom in phase to an extent determined by the differences in the effective lengths of the ray paths traveled by beams 4a, 4c, 4d' and 4d''. These two measuring waves are transmitted via respective leads 18 and 19 to other inputs of phase comparators 20 and 21 whose outputs are connected by leads 22 and 23 to a calculator 24. The latter, taking the various ray-path lengths into account, computes the thickness and the refractive index of vitreous layer 2a, and of similar layers subsequently deposited, as more fully described hereinafter. It should be noted that differences in the lengths of the electrical paths 7, 18, 19 are not very significant at the relatively low beat frequency of about 2 MHz.

Let us consider, for the moment, a test object similar to that shown at 1, 2a which has a wall thickness S and a uniform refractive index $n_1$; the index of the surrounding medium (e.g. air) will be designated $n_0$. It can be shown that, for a given angle of incidence $\alpha$, the change $\Delta l$ in the length of the ray path due to the introduction of the test object is related to parameters S, $n_1$, $n_0$ and $\alpha$ by the following relationship:

$$\Delta l(\alpha) = 2S\left(\frac{n_1}{\sqrt{1 - \frac{n_0^2 \sin^2\alpha}{n_1^2}}} - \frac{n_0}{\cos\alpha}\right) \quad (1)$$

With $\alpha=0$, i.e. for rays incident perpendicularly to the axis, equation (1) reduces to $$\Delta l(0) = 2S(n_1 - n_0) \quad (2)$$

The factor 2 in equations (1) and (2) results from the fact that the incident ray traverses the tube wall twice.

While the foregoing equations apply strictly to test objects with parallel planar faces, the inner and outer peripheral surfaces of the tubular workpiece to be examined can be considered to satisfy that condition at the small wavelength of the incident rays.

The phase differences $\Delta\phi$ detected by comparators 20 and 21 are given by $$\Delta\phi = \frac{2\pi\Delta l}{\lambda_0} \quad (3)$$

where $\lambda_0$ is the wavelength of the laser radiation in vacuum.

In order to determine the thickness $S(a)$ and the refractive index $n_1(a)$ of layer $2a$, we proceed as follows:

Prior to the deposition of the first layer $2a$ on tube 1, beams $4d'$ and $4d''$ are transmitted through that tube at respective angles of incidence 0 and $\alpha$, as shown. From the measuring waves emitted by photodiodes 14 and 15, comparators 20 and 21 determine the respective phase differences $\Delta\phi_0(0)$ and $\Delta\phi_0(\alpha)$ which are stored in a memory of calculator 24.

After the deposition of the first layer $2a$ of doped silica, the described procedure is repeated to yield two new values $\Delta\phi_1(0)$ and $\Delta\phi_1(\alpha)$ fed to calculator 24. By subtracting the previously stored phase-difference values from those newly determined, the calculator is able to compute—in accordance with equation (3)—the changes in path length introduced by the deposited layer $2a$ and to determine the unknown variables $S(a)$ and $n_1(a)$ on the basis of equations (1) and (2). In like manner, the thicknesses and refractive indices of each subsequently deposited layer is calculated. If these parameters are found to depart from predetermined values, the process of making the preform can be suitably modified.

In principle, of course, the thickness and the refractive index of the supporting tube 1 itself can also be calculated from the phase differences initially obtained. These values, however, will generally be available in advance.

All the described measurements are advantageously carried out over the full axial length of the test object and, in a selected transverse plane, over its entire circumference. The requisite relative displacement of the test object and external optical elements could be carried out by the tube-rotating and nozzle-shifting drives of the preform-producing mechanism or, if necessary, by other means.

In some instances, especially with relatively short test objects, the apparatus of FIG. 1 can be simplified by the use of a swingable workpiece holder allowing the test object to be rotated about an axis transverse to the direction of the transluminating beam $4d$. Such a modification has been illustrated in FIG. 2 in which the test object is a flat slab 101 of transparent material with parallel planar faces. A holder 125 supporting the test object 101 lets the latter be swung about an axis A, perpendicular to beam $4d$, through an angle of incidence $\alpha'$ for the successive performance of phase-shift measurements analogous to those carried out concurrently in the embodiment of FIG. 1. When the test object 101 is in its full-line position, with the angle of incidence equal to zero, the rays of beam $4d$ transluminate this test object without deflection so as to reach the single photodiode 15 on a path in line with that of the incident rays as indicated at $4e$. When the test object is turned into the phantom-line position corresponding to an angle of incidence $\alpha'$, that path is shifted to a position $4f$ still terminating at the same photodiode 15 which also receives, as before, the bypassing rays of beam $4c$. Two measuring waves successively generated by photodiode 15 are transmitted to the single phase comparator 21 by way of lead 19 for comparison with the reference wave on lead 7; as in the previous embodiment, comparator 21 delivers the detected phase differences via lead 23 to calculator 24 for storage and computation of the parameters to be measured, namely thickness $S$ and refractive index $n$ of test object 101.

In the present instance, the equation to be used for the determination of the path-length difference $\Delta l$ has the form $$\Delta l = S(\sqrt{n^2 - \sin^2\alpha'} - \cos\alpha') \quad (4)$$

which is used by calculator 24, together with equation (3), to compute the desired parameters.

The described procedures are valid only as long as the detected phase differences $\Delta\phi$ are less than $2\pi$, inasmuch as comparators 20 and 21 cannot distinguish between phase angles differing from one another by an even multiple of $\pi$. This will generally not be a problem in the manufacture of a preform, as described with reference to FIG. 1, where the deposited layers $2a$ are of limited thickness. If, however, the thickness of a test object such as slab 101 is substantially greater than wavelength $\lambda_0$, the resulting phase shift may exceed the limit of $2\pi$. In such a case we can still obtain correct results by using more than two transluminating ray paths, as by taking an additional phase-shift measurement with the system of FIG. 2 in a position of test object 101 intermediate those shown in solid and phantom lines. A first measurement, taken in the solid-line position, will provide a reference value stored in calculator 24 which will be subtracted from the phase shifts detected in the two other positions to provide, again, two equations from which the parameters $S$ and $n$ can be determined. It is only necessary to observe that the angles separating the successive measuring positions are small enough to provide incremental phase shifts of less than $2\pi$.

Although beams $4a$ and $4c$ avoid the test object in both FIGS. 1 and 2, such avoidance—while preferred—is not absolutely necessary in all instances. If, for example, a body of uniform refractive index (such as slab 101) is held stationary while being transluminated by beams $4d'$ and $4d''$ in the system of FIG. 1, beam $4a$ could also pass through the same body on its way to photodiode 6 for producing the reference wave on lead 7.

We claim:

1. A method of measuring the thickness and the refractive index of a test object with substantially parallel major surfaces transparent to luminous radiation, comprising the steps of:
   (a) generating a first and a second monochromatic beam of luminous radiations of constant frequencies differing slightly from each other;
   (b) photoelectrically deriving from said first and second beams an electrical reference wave of a beat frequency corresponding to the difference between the beam frequencies:
   (c) transluminating the test object with rays of said second beam at a first angle of incidence;
   (d) photoelectrically mixing rays of said second beam, passed by the test object in step (c), with rays of said first beam, traveling over a different path, to derive therefrom a first electrical measuring wave of the same beat frequency as said reference wave but differing in phase therefrom to an extent dependent on the thickness and the refractive index of the test object;

(e) determining the phase difference between said reference wave and said first measuring wave;

(f) repeating steps (c) and (d) with a second angle of incidence, differing from said first angle, to derive two rays of said first and second beams a second electrical measuring wave of the same frequency as said reference wave and differing in phase therefrom;

(g) determining the phase difference between said reference wave and said second measuring wave; and (h) calculating the thickness and the refractive index of the test object from the values obtained in steps (e) and (g).

2. A method as defined in claim 1 wherein said first and second monochromatic beams are obtained from a laser subjected to a magnetic field causing a Zeeman effect.

3. A method as defined in claim 1 wherein said first angle of incidence is zero.

4. A method as defined in claim 1 wherein steps (c), (d) and their repetition in step (f) are performed simultaneously with different rays of said second beam transmitted through the test object at said first and second angles.

5. A method as defined in claim 1 wherein the test object is rotated relatively to the ray path of said second beam between steps (c) and (f) to change from said first angle to said second angle.

6. A method as defined in claim 1 wherein the test object is a support of vitreous material in the process of being coated with successive layers of similar vitreous material possibly differing in refractive index from one layer to the other, steps (c) through (h) being initially performed on said support alone and being subsequently repeated upon the deposition of each layer thereon.

7. A method as defined in claim 6 wherein the frequencies of said first and second beams lie in the THz range and are separated from each other by a difference of a few MHz.

8. A method as defined in claim 7 wherein said first and second beams are generated by a common laser.

9. A method as defined in claim 1 wherein said different path bypasses the test object.

10. A method as defined in claim 1 wherein step (b) is performed by mixing rays of said first and second beams passing entirely outside the test object.

11. An apparatus for measuring the thickness and the refractive index of a test object with substantially parallel major surfaces transparent to luminous radiation, comprising:

a holder for the test object to be examined;

a source of monochromatic first and second beams of luminous radiation of constant frequencies differing slightly from each other;

first photoelectric means positioned to receive rays from said first and second beams to derive therefrom an electrical reference wave of a beat frequency corresponding to the difference between the beam frequencies;

optical means for guiding rays of said first beam along a first path and for guiding rays of said second beam along a second and a third path traversing the test object at a first and a second angle of incidence, respectively;

second photoelectric means positioned to receive rays from said first, second and third paths to derive from the rays of said first and second paths a first electrical measuring wave and from the rays of said first and third paths a second electrical measuring wave both having the same beat frequency as said reference wave but differing therefrom in phase to an extent respectively dependent on said first and second angles of incidence, the phase differences between said reference wave and said measuring waves being both a function of the thickness and the refractive index of the test object;

phase-comparison means connected to said first and second photoelectric means for determining said phase differences; and arithmetic means connected to said phase-comparison means for calculating said thickness and refractive index.

12. An apparatus as defined in claim 11 wherein said source is a Zeeman-effect laser emitting a composite beam containing said first and second monochromatic beams.

13. An apparatus as defined in claim 12, further comprising beam-splitting means directing part of said composite beam to said first photoelectric means, said optical means including frequency-separating means positioned to receive another part of said composite beam from said beam-splitting means for directing rays from said first and second beams to said first and second optical means, respectively.

14. An apparatus as defined in claim 13 wherein said frequency-separating means comprises a quarter-wave plate followed by a polarizer.

15. An apparatus as defined in claim 13 wherein said first path bypasses the location of the test object.

16. An apparatus as defined in claim 15 wherein said optical means includes a further beam splitter simultaneously directing respective rays of said second beam, coming from said frequency-separating means, onto said second and third paths, said second photoelectric means including two photodectors respectively positioned to intercept rays from said second and third paths downstream of the test object.

17. An apparatus as defined in claim 15 wherein said holder is displaceable to swing the test object about an axis transverse to a trajectory for rays of said second beam coming from said frequency-separating means, said second and third paths branching off said trajectory in different angular positions of said holder.

18. An apparatus as defined in claim 13 wherein said first photoelectric means receives said part of said composite beam from said beam-splitting means over a path excluding the test object.

* * * * *